(12) United States Patent
Dhepe et al.

(10) Patent No.: US 9,988,413 B2
(45) Date of Patent: Jun. 5, 2018

(54) PROCESS FOR CONVERSION OF HEMICELLULOSE INTO C5 SUGARS USING IONIC LIQUIDS

(71) Applicant: COUNCIL OF SCIENTIFIC & INDUSTRIAL RESEARCH, New Delhi (IN)

(72) Inventors: Paresh Laxmikant Dhepe, Maharashtra (IN); Babasaheb Mansub Matsagar, Maharashtra (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days. days.

(21) Appl. No.: 15/112,813

(22) PCT Filed: Jan. 21, 2015

(86) PCT No.: PCT/IN2015/050007
§ 371 (c)(1),
(2) Date: Jul. 20, 2016

(87) PCT Pub. No.: WO2015/111086
PCT Pub. Date: Jul. 30, 2015

(65) Prior Publication Data
US 2016/0347781 A1    Dec. 1, 2016

(30) Foreign Application Priority Data

Jan. 21, 2014   (IN) .......................... 0187/DEL/2014

(51) Int. Cl.
*C07H 1/08*   (2006.01)
*C07H 3/02*   (2006.01)
*C07D 307/50* (2006.01)

(52) U.S. Cl.
CPC ............. *C07H 1/08* (2013.01); *C07D 307/50* (2013.01); *C07H 3/02* (2013.01)

(58) Field of Classification Search
CPC ....................................................... C07H 1/08
See application file for complete search history.

(56) References Cited

U.S. PATENT DOCUMENTS 8,575,374 B1    11/2013  Delong et al.
2014/0004563 A1*  1/2014  Paripati .................. C07K 1/145
                                                435/68.1

FOREIGN PATENT DOCUMENTS

WO    WO 2013/192572    * 12/2013

OTHER PUBLICATIONS

InCl2Oionic liquid catalytic system for efficient and selective conversion of cellulose into 5-hydroxymethylfurfural. Hu Li et al. RSC Advances, vol. 3, pp. 3648-3654, 2013.*
InCl3-ionic liquid catalytic system for efficient and selective conversion of cellulose into 5-hdroxymethylfurfural Hu Li et al. RSC Advances, vol. 3, pp. 3648-3654 (Year: 2013).*
Amarasekara et al., "Hydrolysis and Decomposition of Cellulose in Bronsted Acidic Ionic Liquids Under Mild Conditions", Ind. Eng. Chem Res, 2009, vol. 48, pp. 10152-10155.
Li et al., "Acid in Ionic Liquid: An Efficient System for Hydrolysis of Lignocellulose", Green Chem., 2008, vol. 10, pp. 177-182.
A. Amarasekara, Degradation of Cellulose in Dilute Aqueous Solutions of Acidic Ionic Liquid 1-(1-Propylsulfonic)-3-methylimidazolium Chloride, and p-Toluenesulfonic Acid at Moderate Temperatures and Pressures, Industrial and Engineering Chemistry Research, Nov. 2, 2011, vol. 5, No. 21, pp. 12276-12280.
Z. Conrad Zhang, "Catalytic Transformation of Carbohydrates and Lignin in Ionic Liquids", Wiley Interdisciplinary Review, Energy and Environment, John Wiley & Sons, Inc., Nov. 1, 2013; vol. 2, No. 6, pp. 655-672.

* cited by examiner

*Primary Examiner* — Douglas B Call
(74) *Attorney, Agent, or Firm* — Baker & Hostetler LLP (57) ABSTRACT

The present invention discloses one pot process for the conversion of hemicellulose into C5 sugars using ionic liquids in water media.

7 Claims, 6 Drawing Sheets

PROCESS FOR CONVERSION OF HEMICELLULOSE INTO C5 SUGARS USING IONIC LIQUIDS

CROSS REFERENCE TO RELATED APPLICATIONS

This application is a National Stage of International Application No. PCT/IN2015/050007, filed on Jan. 21, 2015, which claims priority to Indian patent application no. 0187/DEL/2014, filed on Jan. 21, 2014, the disclosures of which are incorporated by reference in their entirety.

FIELD OF THE INVENTION

The present invention relates to a one pot process for the conversion of hemicellulose into C5 sugars using ionic liquids in water media.

BACKGROUND AND PRIOR ART

Hemicellulose, a polysaccharide is made up of xylose, arabinose (C5 sugars) galactose mannose and other sugars. It is the second most abundant component of plant derived biomass after cellulose. Hemicellulose can be hydrolyzed to C5 sugars (xylose and arabinose) and further those can be dehydrated into furfural, an industrially important chemical.

The typical reaction is shown above in Scheme A.

Xylose, a C5 sugar is an important platform chemical, which upon hydrogenation gives xylitol that finds application as a sweetener in food and pharmaceutical industries. Dehydration of xylose gives another key chemical, furfural that can act as building block for the synthesis of furfuryl alcohol, furanic acid, methyl furan and tetrahydrofuran (THF). Xylose can also undergo oxidation reaction to yield xylonic acid which has a multiple application.

U.S. Pat. No. 8,575,374 B1 describes the use of an ionic liquid acid catalyst for the hydrolysis of cellulose into reducing sugars and other degradation products. It uses the following ionic liquids:

But the process is a two step process.

Article titled, "Hydrolysis and Decomposition of Cellulose in Brönsted Acidic Ionic Liquids Under Mild Conditions" by Ananda S. Amarasekara in IND ENG CHEM RES 11/2009 reports that Cellulose dissolves in Brönsted acidic ionic liquids 1-(1-propylsulfonic)-3-methylimidazolium chloride and 1-(1-butylsulfonic)-3-methylimidazolium chloride up to 20 g/100 g ionic liquid by gentle mixing at room temperature.

Article titled, "Acid in ionic liquid: An efficient system for hydrolysis of lignocellulose" Changzhi Li, Qian Wang and Zongbao K. Zhao in Green Chem., 2008,10, 177-182 reports an efficient system for hydrolysis of lignocellulosic materials with improved total reducing sugars (TRS) yield under mild conditions. TRS yields were up to 66%, 74%, 81% and 68% for hydrolysis of corn stalk, rice straw, pine wood and bagasse, respectively, in $C_4$mimCl in the presence of 7 wt % hydrogen chloride at 100° C. under atmospheric pressure within 60 min. Different combinations between ionic liquids, such as $C_6$mimCl, $C_4$mimBr, AmimCl, $C_4$mim$HSO_4$, and Sbmim$HSO_4$, and acids, including sulfuric acid, nitric acid, phosphoric acid, as well as maleic acid, afforded similar results albeit longer reaction time was generally required comparing with the combination of $C_4$mimCl and hydrochloric acid.

But the prior art process provide poor yields of reducing sugars.

To overcome the drawbacks of the prior arts, it is critical to synthesize xylose from hemicellulose with high efficiency. The process provided should be advantageous with respect to industrial applicability and also result in higher selectivity and yields for preferred products.

OBJECTIVE OF THE INVENTION

The main object of the present invention is to provide a one pot, one step process for the conversion of hemicellulose into C5 sugars using ionic liquids in water media.

SUMMARY OF THE INVENTION

Accordingly, the present invention provides a one pot process for conversion of substrate to C5 sugars, wherein the process comprises: mixing substrate, solvent and ionic liquid catalyst at a temperature in the range of 130 to 180° C. for a time in the range of 10 min to 12 h to obtain C5 and C6 sugars, wherein the process has selectivity in the range of 75-95% towards C5 sugars.

Alternatively, the present invention provides a one pot, one step ionic liquid catalyzed process for conversion of substrate to C5 sugars with selectivity in the range of 75-95% towards C5 sugars wherein the said process comprises the step of mixing substrate, solvent and ionic liquid catalyst at a temperature in the range of 130 to 180° C. for time in the range of 10 min to 12 h to obtain C5 and C6 sugars.

In an embodiment of the present invention substrate is selected from Rice Husk-1, Rice Husk-2, Wheat straw, hemicellulose and Bagasse.

In one embodiment of the present invention solvent used is water.

In another embodiment of the present invention ionic liquid catalyst is selected from 1-methyl-3-(3-sulfopropyl)-imidazolium hydrogensulfate, 1-methyl-3-(3-sulfopropyl)-imidazolium para-toluenesulfonate, 1-methyl-3-(3-sulfopropyl)-imidazolium chloride or 1-butyl-3-methylimidazolium chloride.

Still in another embodiment of the present invention ionic liquid catalyst is preferably 1-methyl-3-(3-sulfopropyl)-imidazolium hydrogensulfate.

Still in another embodiment of the present invention C5 sugars are selected from xylose, arabinose; furfural and oligomers.

Still in another embodiment of the present invention C5 sugars are preferably xylose and arabinose with yields in the range of 70% -95%.

Still in another embodiment of the present invention C6 sugars are selected from glucose and fructose with yields in the range of 10 to 15%.

Still in another embodiment of the present invention the process is carried out in batch mode.

BRIEF DESCRIPTION OF THE DRAWINGS

FIG. 1: Time study for the conversion of hemicellulose using 1-methyl-3-(3-sulfopropyl)-1H-imidazol-3-ium 4-methylbenzenesulfonate Brnsted acidic ionic liquids. Reaction condition: Hemicellulose 0.6 g, water 60 mL, temp 160° C. and catalyst 0.24 g.

FIG. 2: Substrate to catalyst ratio for the hemicellulose conversion using 1-methyl-3-(3-sulfopropyl)-1H-imidazol-3-ium 4-methylbenzenesulfonate catalyst. Reaction condition: Hemicellulose 0.6 g, water 60 mL, time 1 h, temp 160° C.

FIG. 3: $^1$HNMR of [$C_3SO_3HMIM$] [$HSO_4$] Brnsted acidic ionic liquids.

FIG. 4: $^{13}$CNMR (DEPT) of [$C_3SO_3HMIM$] [$HSO_4$] Brnsted acidic ionic liquids.

FIG. 5: $^{13}$CNMR of [$C_3SO_3HMIM$] [$HSO_4$] Brnsted acidic ionic liquids

FIG. 6: UV-vis spectra for measuring Hammett acidity function ($H_o$) of various catalysts.

DETAILED DESCRIPTION OF THE INVENTION

Figure 7:
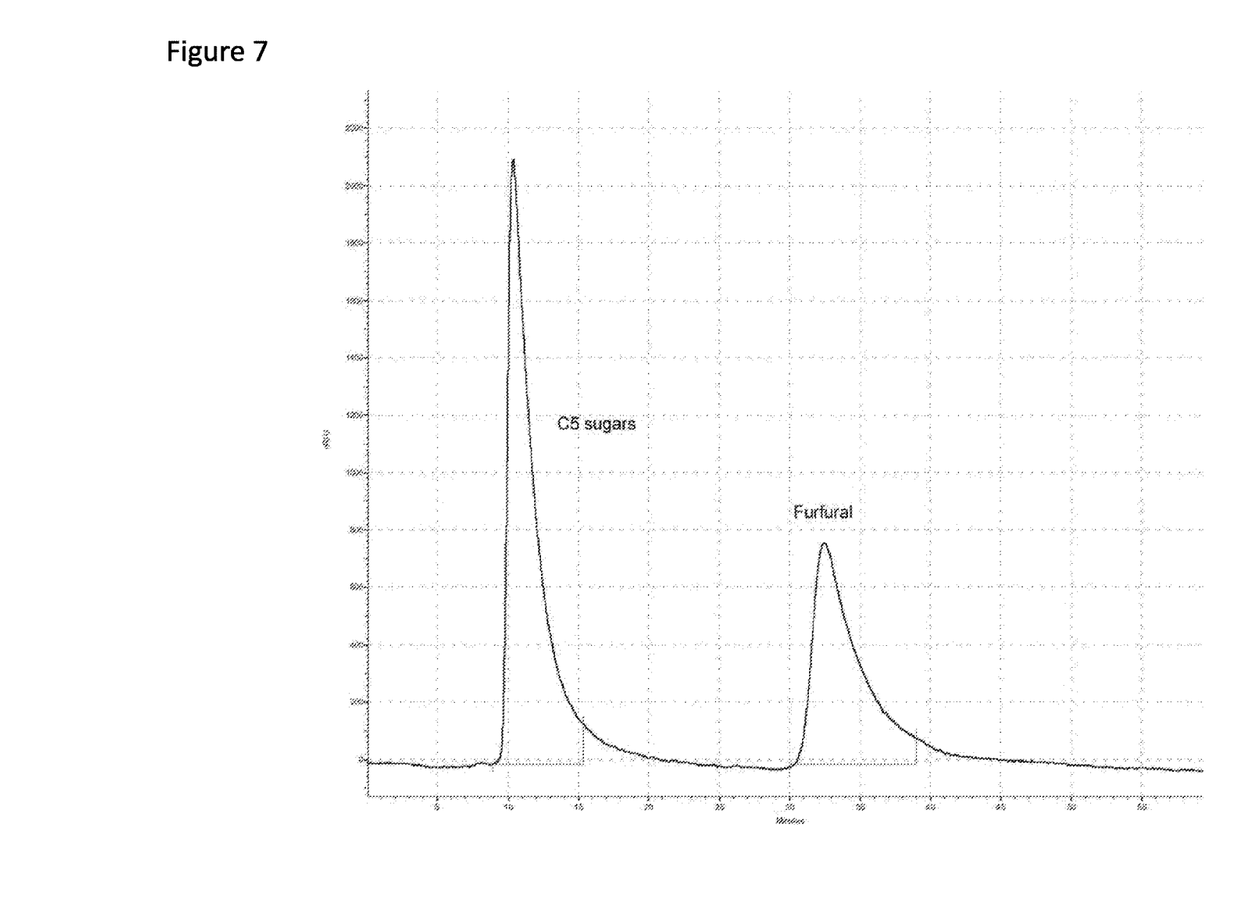
FIG. 7. HPLC profile of standards C5 sugar (xylose+arabinose) and furfural.
Figure 8:
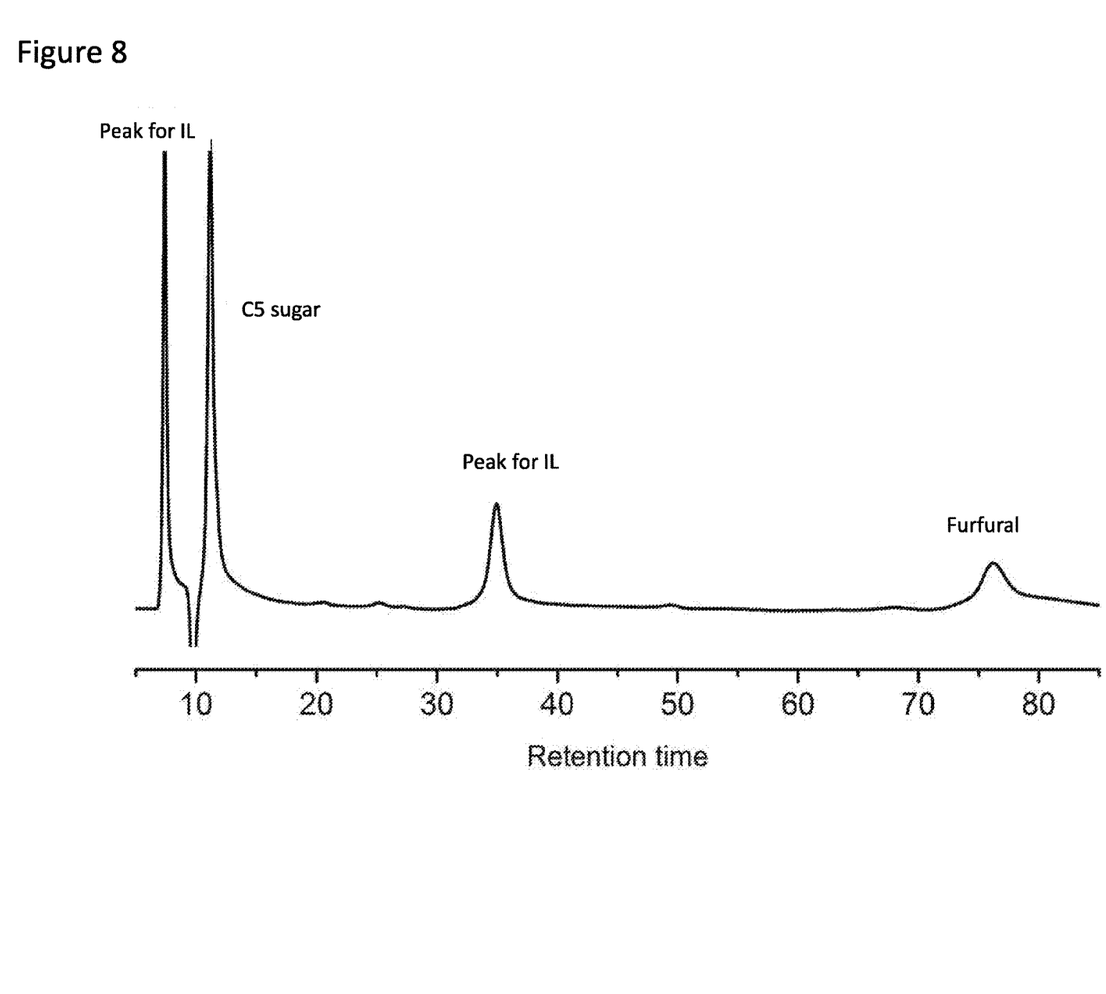
FIG. 8. HPLC Profile of reaction mixture using [C3SO3HMIM][PTS] ILs.

The present invention provides a one pot process for the conversion of hemicellulose into C5 sugars using ionic liquids in water media.

The present invention provides a one pot, single step ionic liquid catalyzed process for conversion of hemicellulose to C5 sugars with >50% selectivity towards C5 sugars comprising the step of mixing Hemicellulose/substrate, solvent and ionic liquid catalyst at a temperature in the range of 130 to 180° C.; time in the range of 10 min to 12 h to obtain the desired product.

The present invention provides a process wherein the substrate is selected from Rice Husk-1 (procured from Mr. Narayan P. Singhania, M. K. Enterprises, Mukhya marg, Jharsujnda, Odisha 768201), Rice Husk-2 (procured from Nutan Kumar T P, S/o H Purushotam Neelamma Nilaya Sebinakere post Thirthahalli (T) Shimoga (D) 577432, Karnataka), Wheat straw (procured from Deepak Kumar Singh, Village & Post Bhaupur Tehsil Kerakatt, Dist. Jaunpur, 222136, Uttar Pradesh) or Bagasse (procured from Matsagar Mansub S., At. Jarul, Post Rotegaon, Dist. 3701, Aurangabad, Maharashtra); products are C5 sugars selected from xylose, arabinose, furfural and oligomers or C6 sugars selected from glucose, fructose (with >8% yields).

The present invention provides a process wherein hemicellulose yields C5 sugars as products preferably xylose and arabinose with >70% yields and preferably >85% yields.

The present invention provides a process wherein the process is carried in batch mode; solvent is preferably water and ionic liquids is preferably in liquid state at room temperature or at least below reaction temperature.

The present invention provides a process using ionic liquid wherein, ionic liquid is selected from, as summarized below in Table A:

TABLE A

| Ionic liquids |
|---|
| [$C_3SO_3HMIM$][$HSO_4$] |
| [$C_3SO_3HMIM$][Cl] |
| [$C_3SO_3HMIM$][PTS] |
| [BMIM][Cl] |

The present invention provides a process using ionic liquid wherein, ionic liquid is preferably 1-methyl-3-(3-sulfopropyl)-imidazolium hydrogensulfate.

In an aspect the present invention provides a process wherein ionic liquid catalyst is Bronsted acidic ionic liquid selected from 1-methyl-3-(3-sulfopropyl)-imidazolium hydrogensulfate, 1-methyl-3-(3-sulfopropyl)-imidazolium para-toluenesulfonate, 1-methyl-3-(3-sulfopropyl)-imidazolium chloride.

EXAMPLES

The following examples are given by way of illustration of the working if the invention is actual practice and shall not be construed to limit the scope of the present invention in anyway.

Example 1

Experimental

Ionic Liquids:
Brnsted acidic ionic liquids (Table: A) were synthesized using known procedure and characterized using $^1$HNMR, $^{13}$CNMR and CHNS analysis. The stability of the ionic liquids was checked by TGA study.

Catalytic Reaction:
All of the catalytic reactions were performed in batch mode using a high-temperature and high-pressure reactor (Parr autoclaves, USA) equipped with a Teflon liner. In a typical reaction, 0.6 g (4.54 mmol) of solid hemicellulose was charged in the reactor and then 60 mL of water and 0.24 g of catalyst were added to it (substrate/catalyst=2.5 (wt/wt)). The reactions were performed at a desired reaction temperature for a definite time under mechanical stirring (800 rpm). After the reaction, the reactor was cooled to room temperature under flowing water.

Results
For the conversion of hemicellulose in to C5 sugars (xylose and arabinose) and furfural Brnsted acidic ionic liquids were used and the results are compared with mineral acid ($H_2SO_4$) in Table 1.

As seen from Table: 1, when hardwood hemicellulose (xylan from birchwood) hydrolysis reactions were conducted in the presence of water at 160° C., the BAIL [$C_3SO_3HMIM$]$HSO_4$ Kindly check] was very selective in forming C5 sugars (xylose+arabinose), with >87% yield within 1 h of reaction time. Similarly, other BAILs evaluated in this study, such as [C3SO3HMIM][PTS] (>76%) and [C3SO3HMIM][Cl] (75%) also showed good activity for C5 sugar (xylose+arabinose) formation. Among all of the catalysts evaluated in this study, >99% conversion was observed for xylan (hemicellulose).

The Substrate/Catalyst (wt/wt) ratio used was 2.5. (FIG. 2)

Example 2

Synthesis of Brnsted Acidic Ionic Liquids (Catalyst)

a) 1-methyl-3-(3-sulfopropyl)-imidazolium para-toluenesulfonate, [$C_3SO_3HMIM$][PTS]:

1-methyl imidazole, 7.625 mmol and 1, 3-propane sultone, 7.625 mmol were dissolved in 10 mL toluene and refluxed at 110° C. for 16 h in a round bottom flask under stirring. The product; the zwitter ion was formed in quantitative yield and was precipitated out as a white solid. The white precipitate formed was isolated by filtration, and dried and used as such for the next step. Synthesis of IL was accomplished by mixing equimolar quantities of p-toluenesulfonic acid (PTSA) and zwitter ion. The resulting solution was stirred at 70° C. for 24 h. During this time the solids react, resulting in the formation of the BAIL. The color of the BAIL was pale yellow.

Characterization Results
1H NMR (D2O, 200 MHz): δ 8.60 (s, 1H), 7.53 (d, 2H), 7.39 (s, 1H), 7.37 (s, 1H), 7.24 (d, 2H), 4.21 (t, 2H), 3.74 (s, 3H), 2.78 (t, 2H) 2.25 (s, 3H), 1.90 (m, 2H); 13C NMR (D2O, 50 MHz): δ (ppm): 142.42, 139.43, 136.09, 129.40, 125.31, 123.72, 122.14, 47.69, 47.17, 35.66, 25.05, 20.44.

Microanalysis: the approximate % element by microanalysis is C (43), H (5.3), N (7.5) and S (15). Calculated element % C (60.4), H (5.2), O (17.2), P (5.5), and S (11.5).

b) 1-methyl-3-(3-sulfopropyl)-imidazolium hydrogensulfate, [$C_3SO_3HMIM$][$HSO_4$]:

The synthesis procedure is same as mentioned above. However, in place of PTSA equimolar quantities of sulphuric acid and zwitter ions were mixed together. Rest procedure is same to yield BAIL.

Characterization Results
1H NMR (D2O, 200 MHz): δ 8.66 (s, 1H), 7.42(s, 1H), 7.35 (s, 1H), 4.26 (t, 2H), 3.79 (s, 3H), 2.82 (t, 2H), 2.21 (m, 2H);
13C NMR (D2O, 50 MHz), δ 13.16, 123.74, 122.16, 47.7, 47.16, 35.66, 25.04.

Microanalysis: the approximate % element by microanalysis is C (24.2), H (6.5), N (7.2) and S (20.7). Calculated element % C (27.8), H (4.6); N (9.3), O (37), and S (21.2).

c) 1-methyl-3-(3-sulfopropyl)-imidazolium chloride, [$C_3SO_3HMIM$][Cl]:

1-Methyl imidazole and 1,3-propanesultone (7.625 mmol each) were dissolved in 10 mL toluene and refluxed at 110° C. in a RB flask for 24 h under constant stirring. The product; the zwitter ion was formed in quantitative yield and was precipitated out as a solid. The precipitate formed was isolated by filtration, and dried and used as such for the next step. Equimolar quantities of HCl was added to this precipitate and heated at 85° C. for 24 h. This results in the formation of the BAIL.

Characterization Results
1H NMR (D2O, 200 MHz) δ 8.63 (s, 1H), 7.40 (s, 1H), 7.32 (s, 1H), 4.24 (t, 2H), 3.77 (s, 3H), 2.80 (t, 2H), 2.19 (m, 2H);
13C NMR (D2O, 50 MHz), δ 136.2, 123.7, 122.2, 47.73, 47.2, 35.7, 25.1.

Microanalysis: the approximate % element by microanalysis is C (31.75), H (6.2), N (11.5) and S (12.6). Calculated element % C (34.9), H (5.44), Cl (14.7), N (11.6), O (19.9) and S (13.3).

d) 1-butyl-3-methyl imidazolium chloride, [BMIM][Cl]:

In a typical synthesis a solution of 1-chlorobutane (108 mmol) and N-methyl imidazole (108 mmol) was refluxed in round bottom flask at 343K for 24 h under inert atmosphere. After 24 h the reaction mixture showed two distinct layers. The upper layer containing unreacted starting material was decanted and bottom layer was extracted with ethyl acetate (a volume approximately equal to half that of bottom layer). This procedure was repeated thrice. Washing with ethyl acetate should suffice to remove any untreated starting material from bottom phase. The remaining solvent from crude ionic liquid was distilled off on rotavapour and the product was dried under high vacuum. Dried IL showed slightly yellow appearance.

Characterization Results
1H NMR (D2O, 200 MHz) δ 8.6 (s, 1H), 7.37 (s, 1H), 7.33 (s, 1H), 4.10 (t, 2H), 3.8 (s, 3H), 1.75 (m, 2H), 1.2 (m, 2H) 0.82 (t, 3H);

13C NMR (D2O, 50 MHz), δ 123.5, 122.2, 49, 35.7, 31.3, 18.8, 12.7.

Microanalysis: the approximate % element by microanalysis is C (50.3), H (9) and N (15). Calculated element % C (55), H (8.6), Cl (20.3) and N (16).

Catalyst Recycle Study:

Two catalyst [C3SO3HMIM][HSO4] and [C3SO3HMIM][PTS] BAILs were recovered and characterized by 1H NMR and also recycle study were carried out after carrying out typical reaction under following reaction conditions: Substrate (beechwood), 0.6 g; [C3SO3HMIM][PTS], 0.24 g; water 60 mL; 160° C.; 1 h. After completion of a reaction, water is removed by rotavap and after that 2 mL of water is added in to it and then slowly acetone (30 mL) was added to give light white color solution. Up on excess addition of acetone, light white color disappears. The solution was kept under static condition for a while. Afterwards, the acetone layer is decanted leaving viscous liquid at the bottom of a container. This liquid contains ionic liquid which was used in recycle study. The acetone layer contains sugars. By this method we could recover ca. 65% ionic liquid and the remaining 35% ionic liquid is present in acetone layer because of its partial solubility, the sugar yield decrease by 20% recovered from acetone layer. The separation of ionic liquids from sugar solution or vice versa is challenging problem that requires further study. In the recycle study, recovered BAIL was subjected to next reaction with following charge: hemicellulose (beechwood) 0.6 g; IL, 0.16 g; water, 60 mL; the reaction was done for 1 h at 160° C.

Example 3

Selective conversion of different crop wastes is also carried out using BAILs and the results are shown in following table.

Reactions were carried out using 1-methyl-3-(3-sulfopropyl)-1H-imidazol-3-ium sulphate {[$C_3SO_3HMIM$] [$HSO_4$]} ionic liquid catalyst.

TABLE 1

Catalytic results of hemicellulose conversion
Reaction condition:
Crop waste 0.6 g, water 60 mL, time 1 h, temp 160° C. and catalyst 0.24 g
Cellulose present in crop waste also converted in to C6 sugar (glucose) but the yield for glucose and fructose is low which is around 10-15%.

| | | | YIELD (%) | |
|---|---|---|---|---|
| SR. NO | CATALYST | OLIGOMER | XYLOSE + ARABINOSE (C5 SUGARS) yield % (selectivity, % in bracket) | FURFURAL |
| 1 | Without catalyst | 50.1 | 14.4 (20) | 0 |
| 2 | HUSY (Si/Al = 15) - solid acid catalyst | 23 | 37 (40) | 0 |
| 3 | H-MOR (Si/Al = 10) - solid acid catalyst | 33 | 22 (35) | 0 |
| 4 | $H_2SO_4$ | 0 | 50 (50) | 07 |
| 5 | 1-methyl-3-(3-sulfopropyl)-1H-imidazol-3-ium sulphate | 0 | 88 (88) | 10 |
| 6 | 1-methyl-3-(3-sulfopropyl)-1H-imidazol-3-ium 4-methylbenzenesulfonate | 6 | 77 (77) | 11 |
| 7 | 1-methyl-3-(3-sulfopropyl)-1H-imidazol-3-ium chloride | 0 | 75 (75) | 07 |
| 8 | 3-butyl-1-methyl-1H-imidazol-3-ium chloride | 0 | 32 (32) | 0 |

TABLE 2

Additional examples on Brønsted acidic ionic liquid catalyzed reactions:
Reaction condition: Hemicellulose 0.6 g, water 60 mL, time 1 h,
temp 160° C. and catalyst 0.24

| | | Yield (%) | | |
|---|---|---|---|---|
| Sr. No | Catalyst | Oligomer | Xylose + arabinose (C5 sugars) | Furfural |
| 1 | 1-methyl-3-(3-sulfopropyl)-1Hbenzo[d]imidazole-3-ium 4-methylbenzenesulfonate | — | 73 | 7 |
| 2 | N,N,N-triethyl-3-sulfopropane-1-aminium 4-methylbenzenesulfonate | 12 | 39 | 6 |

TABLE 2-continued

Additional examples on Brønsted acidic ionic liquid catalyzed reactions:
Reaction condition: Hemicellulose 0.6 g, water 60 mL, time 1 h,
temp 160° C. and catalyst 0.24

| Sr. No | Catalyst | Yield (%) | | |
|---|---|---|---|---|
| | | Oligomer | Xylose + arabinose (C5 sugars) | Furfural |
| 3 | Tri-phenyl (3-sulfopropyl) phosphonium 4-methyl benzenesulfonate | 20 | 25 | 1 |
| 4 | N,N,N-triethyl-3-sulfopropane-1-aminium hydrogen sulphate | 17 | 29 | 3.3 |

TABLE 3

CHNS analysis:

| [C₃SO₃HMIM][HSO₄] | Theoretical | Observed |
|---|---|---|
| C % | 27.8 | 30 |
| H % | 4.6 | 6 |
| N % | 9.2 | 10 |
| S % | 21.2 | 19.5 |

TABLE 4

Catalytic results for the selective conversion of crop waste into C5 sugars xylose + arabinose

| | | Yield % | |
|---|---|---|---|
| Sr. No. | Substrate | xylose + arabinose | Furfural |
| 1 | Rice Husk-1 | 73 | 6 |
| 2 | Rice Husk-2 | 93 | 8 |
| 3 | Wheat Straw | 87 | 6 |
| 4 | Bagasse | 91 | 9 |

Prior Art Comparison

| Ref | Substrate (g) | Catalyst | Solvent | Time (h) | Temp (° C.) | Yield % |
|---|---|---|---|---|---|---|
| U.S. Pat. No. 8,575,374 | 1st step: 1.5 g cellulose | Ionic liquid: 15 g Bmim Cl | — | — | 100 | — |
| | 2nd step: mixture obtained from 1st step | Ionic liquid: 1 g 1-methyl-3-(butyl-4-sulfonic acid)imidazolium triflat ([MBSIm]Otf) | 0.215 g water (can't be said it is solvent because quantity is too low) | 24 | 100 | 50-55% glucose |
| "Hydrolysis and Decomposition of Cellulose in Brønsted Acidic Ionic Liquids Under Mild Conditions" by Ananda S. Amarasekara in IND ENG CHEM RES 11/2009 | 20 g cellulose | Acidic Ionic liquid: 100 g BAIL | 2 equivalent of water per glucose unit of cellulose | 30 min | 70 | 14% glucose, 65% total reducing sugar |
| "Acid in ionic liquid: An efficient system for hydrolysis of lignocellulose" Changzhi Li, Qian Wang and Zongbao K. Zhao in | 0.2 g corn stalk | Ionic liquid: 4 g C₄mimHSO₄ | 0.02 g water | 5 min | 100 | 23% total reducing sugar |

| Ref | Substrate (g) | Catalyst | Solvent | Time (h) | Temp (° C.) | Yield % |
|---|---|---|---|---|---|---|
| Green Chem., 2008, 10, 177-182 | | | | | | |

Advantages of Invention:

a. A one-pot, one step method.

b. Conversion of hemicelluloses into C5 sugars with high yields (88%).

c. Milder reaction conditions.

d. High furfural yield can be obtained directly from hemicelluloses.

e. Decreased amount of IL needed and less oligomers obtained.

We claim:

1. A single step, one pot process for conversion of a substrate comprising Rice Husk-1, Rice Husk-2, Wheat straw, hemicellulose and Bagasse, to C5 and C6 sugars, the process comprising: mixing the substrate, solvent and ionic liquid catalyst at a temperature in the range of 130 to 180° C. for a time in the range of 10 min to 12 h to obtain C5 and C6 sugars, wherein C5 sugars yields is in the range of 70%-95%, and the ionic liquid catalyst is selected from 1-methyl-3-(3-sulfopropyl)-imidazolium hydrogensulfate, 1-methyl-3-(3-sulfopropyl)-imidazolium para-toluenesulfonate, or 1-methyl-3-(3-sulfopropyl)-imidazolium chloride.

2. The process according to claim 1, wherein the solvent is water.

3. The process according to claim 1, wherein the ionic liquid catalyst is 1-methyl-3-(3-sulfopropyl)-imidazolium hydrogensulfate.

4. The process according to claim 1, wherein the C5 sugars are selected from xylose and arabinose.

5. The process according to claim 1, wherein the C6 sugars are selected from glucose and fructose with yields in the range of 10 to 15%.

6. The process according to claim 1, wherein the process is carried out in batch mode.

7. The process according to claim 1, wherein the ionic liquid catalyst is recovered and reused.

* * * * *